(12) United States Patent
Framroze (10) Patent No.: US 12,312,343 B2
(45) Date of Patent: May 27, 2025

(54) ROTOMERIC ISOMERS OF 4-ALKYL-5-HETEROARYL-3H-1,2-DITHIOLE-3-THIONES

(71) Applicant: ST IP HOLDING AG, Zug (CH)

(72) Inventor: Bomi Framroze, Menlo Park, CA (US)

(73) Assignee: ST IP HOLDING AG, Zug (CH)

( * ) Notice: Subject to any disclaimer, the term of this patent is extended or adjusted under 35 U.S.C. 154(b) by 707 days.

(21) Appl. No.: 17/205,841

(22) Filed: Mar. 18, 2021

(65) Prior Publication Data

US 2021/0206751 A1 Jul. 8, 2021

Related U.S. Application Data

(63) Continuation of application No. PCT/IB2019/001138, filed on Sep. 17, 2019.

(60) Provisional application No. 62/732,867, filed on Sep. 18, 2018.

(51) Int. Cl.
| | |
|---|---|
| *C07D 409/04* | (2006.01) |
| *A61K 9/00* | (2006.01) |
| *A61P 39/06* | (2006.01) |

(52) U.S. Cl.
CPC .......... *C07D 409/04* (2013.01); *A61K 9/0014* (2013.01); *A61K 9/0053* (2013.01); *A61P 39/06* (2018.01)

(58) Field of Classification Search
CPC ..... C07D 409/04; A61P 39/06; A61K 9/0014; A61K 9/0053
See application file for complete search history.

(56) References Cited

FOREIGN PATENT DOCUMENTS

| CN | 105 327 337 A | 2/2016 | |
|---|---|---|---|
| WO | WO-2008110585 A2 * | 9/2008 | ........... A61K 31/195 |
| WO | WO 2018/047002 A1 | 3/2018 | |
| WO | WO 2018/047013 A1 | 3/2018 | |

OTHER PUBLICATIONS

International Search Report and Written Opinion, International Application No. PCT/IB2019/001138 (published under WO 2020/058767 A1), 11 pages (Feb. 12, 2020).

\* cited by examiner

*Primary Examiner* — Joseph K McKane
*Assistant Examiner* — Quincy McKoy
(74) *Attorney, Agent, or Firm* — Hoffmann & Baron, LLP

(57) ABSTRACT

This disclosure provides, among other things, rotomeric isomers of 4-alkyl-5-heteroaryl-3H-1,2-dithiole-3-thiones, complexes of such isomers in which an individual rotomeric form is obtained by stabilization, and compositions comprising an excess of an individual rotomer (a rotomeric excess) as a stabilized complex. The disclosure also relates to methods of making and using: such rotomers and complexes, including methods of treating a human or animal patient with such rotomers or complexes thereof, e.g., to prevent, treat or reduce the symptoms of various disorders such as mucositis, and/or provide protection against oxidative damage in various organs and tissues for a medical purpose.

23 Claims, 4 Drawing Sheets

ROTOMERIC ISOMERS OF 4-ALKYL-5-HETEROARYL-3H-1,2-DITHIOLE-3-THIONES

CROSS REFERENCE TO RELATED APPLICATIONS

This application is a continuation of International Application No. PCT/IB2019/001138, filed on Sep. 17, 2019, which claims the benefit of U.S. Provisional Application 62/732,867, filed 18 Sep. 2018, the entirety of which applications, including their specification, claims and drawings, are expressly incorporated herein by reference.

FIELD

This disclosure relates, among other things, to rotomeric isomers of 4-alkyl-5-heteroaryl-3H-1,2-dithiole-3-thiones, complexes of such isomers in which an individual rotomeric form is obtained by stabilization, and compositions comprising an excess of an individual rotomer (a rotomeric excess) as a stabilized complex. The disclosure also relates to methods of making and using: such rotomers; complexes in which an individual rotomer is obtained by stabilization and present in a rotomeric excess; compositions (including rotomeric pharmaceutical compositions) comprising the rotomers or complexes thereof; methods of regulating the function of human oxidation protective genes by using such rotomers or complexes thereof; and methods of treating a human or animal patient with such rotomers or complexes thereof (e.g., to prevent, treat or reduce the symptoms of various disorders such as mucositis, and/or provide protection against oxidative damage in various organs and tissues for a medical purpose).

The disclosure herein relates to new pharmaceutical formulations, compositions and therapies comprising a population of 4-methyl-5-(pyrazin-2-yl)-3H-1,2-dithiole-3-thione (also known as oltipraz) rotomers enriched in an individual rotomer that may be stabilized in a complex.

BRIEF DESCRIPTION OF THE DRAWINGS

Atoms in FIGS. 2-5 are shown as circles (spheres) marked with "H" for hydrogen, "S" for sulfur, "N" for nitrogen, or "O" for oxygen. Carbon atoms are shown as unmarked circles (spheres).

DISCLOSURE 4-methyl-5-(pyrazin-2-yl)-3H-1,2-dithiole-3-thione, also known as oltipraz, has been disclosed in both the crystalline and amorphous forms. Oltipraz has been described as having various properties, e.g., as an anti-microbial compound that controls schistosomiasis, as an anti-tumor agent, as a chemo-protectant, and as a compound to help control chemo-radiation induced mucositis.

The mechanism of action of the chemo-protective and mucositis controlling effect has been described to be via the up-regulation of the transcription factor, nuclear factor erythroid 2-related factor 2 (Nrf2) protective genes. Nrf2, which is activated by reactive oxygen species (ROS), appears to be a key regulator in oxidative stress gene regulation. Nrf2 is a member of the Cap'n'Collar family of bZIP proteins. Under normal conditions, Nrf2 is bound to its inhibitor, the cytoskeleton-associated protein Keap1, which represses Nrf2 by facilitating its proteasomal degradation. Upon treatment by antioxidants, Nrf2 is released from Keap1 and it initiates the up-regulation of over 2000 antioxidant genes.

Oltipraz has been shown to activate a series of oxidation protective genes in in vitro gene expression assays using pooled human gingival epithelial cells. Gene expression has also been used to show 200 differentially expressed oxidative genes in subjects with COPD (chronic obstructive pulmonary disorder) when compared with healthy smokers and the significant changes in oxidant response genes observed in vivo were reproduced in vitro using primary bronchial epithelial cells from the same donors. [Pierrou, S., Broberg, P., O'Donnell, R. A., Pawlowski, K., Virtala, R., Lindqvist, E. (2007) Expression of Genes Involved in Oxidative Stress Responses in Airway Epithelial Cells of Smokers with Chronic Obstructive Pulmonary Disease. Am. J. of Respiratory and Critical Care Medicine, 175(6), 577-587].

In vitro gene expression has also been studied in human corneal endothelial cells (HCECs) to determine if nuclear oxidative DNA damage increases with age. HCECs respond to this damage by upregulating 4 of 84 of their oxidative stress and DNA damage-signaling genes in an age-dependent manner. [Joyce, N. C., Harris, D. L., Zhu, C. C. Age-Related Gene Response of Human Corneal Endothelium to Oxidative Stress and DNA Damage (2011) Cornea, 52(3), 1641-1649].

Hence, it is widely accepted that gene expression changes observed in in vitro cellular assays have been shown to be representative of physiological oxidation protection conferred to specific organs and tissues.

The chemical structure of oltipraz was optimized for schistosomiasis control by Quantitative Structure Activity Relationship (QSAR) studies. Although oltipraz has recently shown Nrf2 up-regulating activity, whether it is the optimum structure or in an optimal configuration for Nrf2 up regulation, is unknown.

As discussed below, it has been discovered that stable compositions comprising two different rotomers of oltipraz can prepared. The compositions may comprise up to about an 80%, 85%, 90%, 95%, 97% 98% or 99% rotomeric excess of one of the two rotomers, which may be stabilized in the form of an oltipraz-complex. Compositions comprising higher rotomeric excess percentages, e.g., above 90% (i.e., 95% of one rotomer and 5% of the other) may be less stable at higher temperatures because of the relatively low barrier to rotation. As used herein an "oltipraz-complex" means oltipraz dissociably associated (covalently or non-covalently) with a molecule or atom. Such compositions comprising a rotomeric excess of either of the individual rotomers may specifically increase the up-regulation of the transcriptional factor Nrf2 effect, and hence provides oxidation protection from chemo-radiation and immunotherapy induced mucositis in the gastro-intestinal system, including in the oral cavity.

Figure 1:
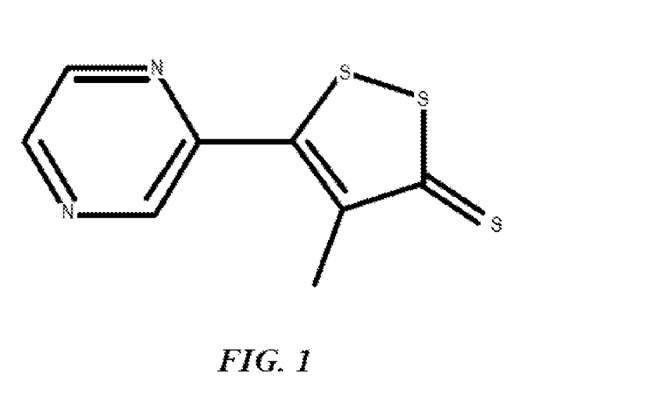
FIG. 1 oltipraz (4-alkyl-5-(pyrazin-2-yl)-3H-1,2-dithiole-3-thione).

Oltipraz (4-alkyl-5-(pyrazin-2-yl)-3H-1,2-dithiole-3-thione) consists of two rings, the pyrazinyl ring and the dithiolethione ring, connected by a carbon-carbon single bond (FIG. 1).

Normally, free rotation is possible around such a carbon-carbon (C—C) bond such that no specific orientation of the two rings is locked and the two rings have been described in an X-ray structure publication as being in a twisted planar configuration in which conjugation between the unsaturation bonds in each ring allows for the lowest energy stable state, as shown in FIG. 1 above. See, Wei, C. H., Structure of 4-Methyl-5-(2-pyrazinyl)-3H-1,2-dithiole-3-thione (Oltipraz), A New Antischistosomal Drug. Acta Cryst. (1983). C39, 1079-1082)

Figure 2:
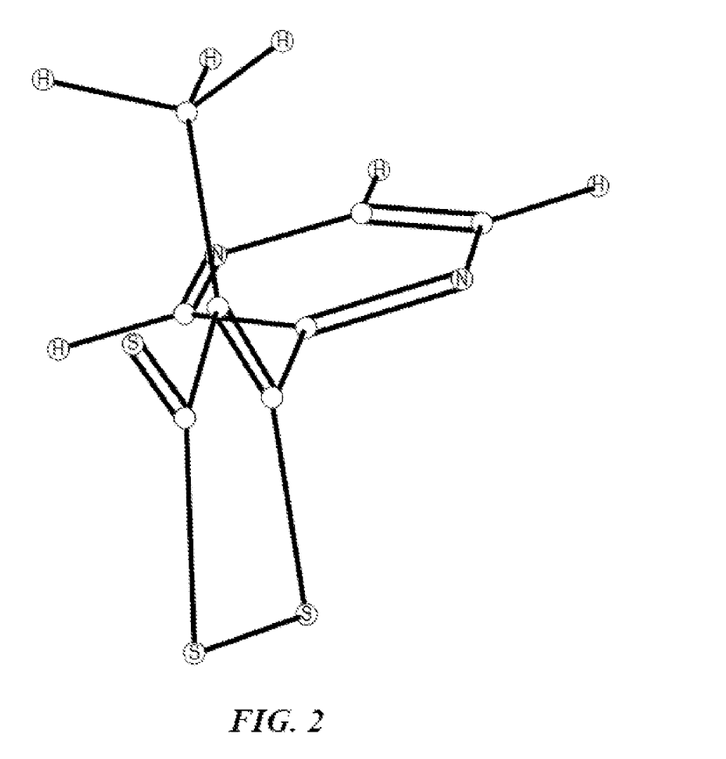
FIG. 2 depicts oltipraz shown in a configuration where its two rings are almost orthogonal to each other.

Using energy minimization computer simulations with the Tinker® tool and common parameter sets such as Amber and MMFF applied, it was discovered that molecules of oltipraz may also be found in a stable configuration where the two rings are almost orthogonal to each other, e.g., as shown in FIG. 2.

Figure 3:
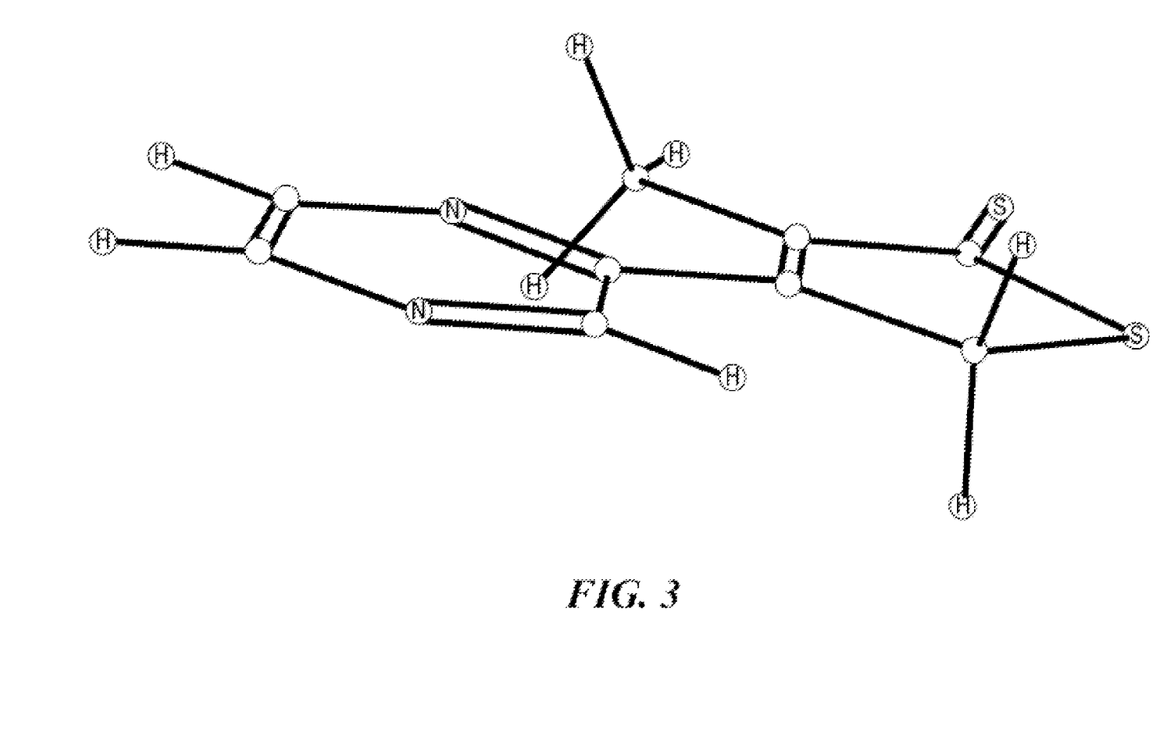
FIG. 3 depicts an oltipraz analog wherein the alpha dithiol sulfur atom is substituted with a carbon atom.

Further computer analysis on analog structures showed that this preferred orthogonal configuration is likely due to sulfur hyperconjugation. Substitution of the alpha dithiol sulfur atom with a carbon atom, which is unable to participate in hyperconjugation, resulted in a planar structure as the minimum energy configuration, with free rotation around the connecting C—C single bond as shown in FIG. 3.

The simulation also showed that an unexpected, unusually high energy barrier exists between one orientation of the two orthogonal rings versus its mirror image, of 14.1 kJ/mol. This may be attributed to the sulfur hyperconjugation effect which needs to be broken to allow rotation along the bond between the two rings. Accordingly, the rotomers are a pair of atropisomers, due to hindered rotation about the bond between the two rings of oltipraz.

The Rotomer Compositions

Figure 4A:
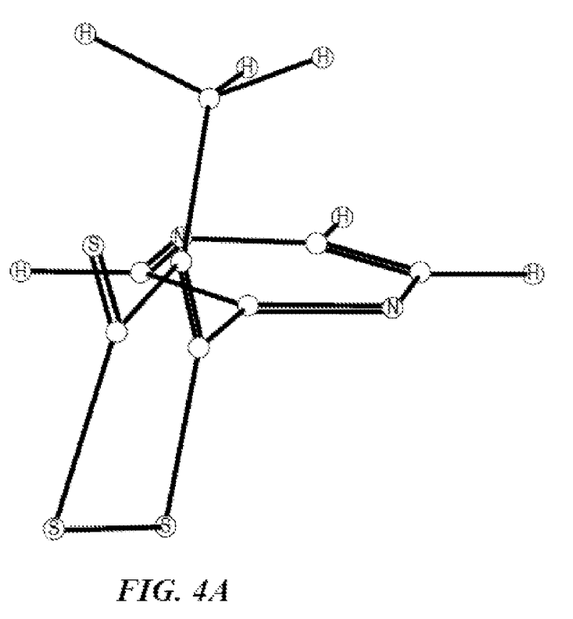
FIG. 4A depicts the positive (+) rotomer of oltipraz.
Figure 4B:
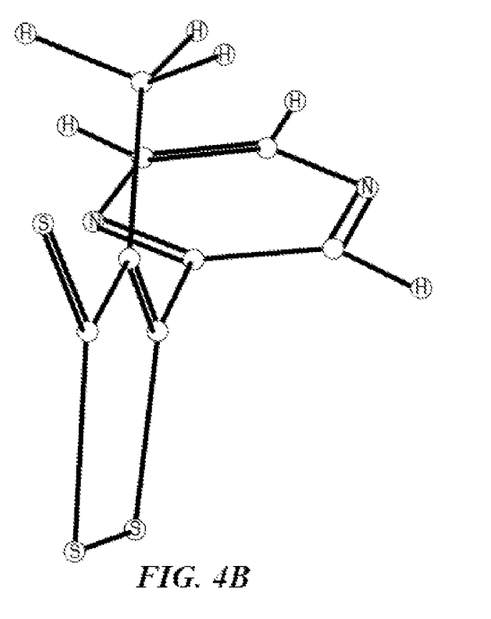
FIG. 4B depicts the negative (−) rotomer of oltipraz.

Two distinct rotomers for oltipraz are thus possible. Each of the two rotomers can be defined as two rings that are orthogonal to each other; the (+)-rotomer is defined by orienting the thione and methyl group on top and the alpha nitrogen of the pyrimidine ring on the right, while the (−)-rotomer has the alpha nitrogen of the pyrimidine ring on the left side (see FIGS. 4A and 4B).

It has been found that preparing an oltipraz-complex in the form of a number of salts as described below yields a composition in which the (+)-rotomer (FIG. 4A) can be present in a rotomeric excess (e.g., up to about 80%). As used herein, the term "rotomeric excess" means the excess of one rotomer over the other as is commonly applied to the term "enantiomeric excess". Thus "rotomeric excess" herein is described as a measurement of the purity of the population of oltipraz rotomers as a whole. It reflects the degree to which a sample contains one rotomer in greater amounts than the other. A meso mixture has a rotomeric excess of 0%, while a single completely
pure rotomer has a rotomeric excess of 100%. So, for
  example, a sample with 70% of one rotomer and 30%
  of the other has a rotomeric excess of 40% (70%-30%).

The relative percent of one isomer over the other can be assigned using the relative intensities of the thione peaks at ~1200 and ~440 cm-1 in an FTIR analysis. The (+) rotomer displays FTIR thione peaks between 420 to 424 and 1210 to 1215 whereas the (−) rotomer shows FTIR thione peaks between 432 to 436 and 1200 to 1205.

Examples of the complexes of oltipraz that may exhibit a rotomeric preference for the (+)-rotomer (see Examples 1 and 3-6 below) include salts resulting from addition or association of a group (e.g., the reversible addition of HCl, alkyl halides or acyl halides) to oltipraz's pyrazinyl ring (e.g., at the alpha nitrogen) yielding a N-substituted pyrazinium ion (with the positive charge most likely centered on the alpha nitrogen of the pyrazinyl group) and an associated anion. Some substituents groups that may be present on a pyrazine ring as the result of salt formation include, but are not limited to hydrogen, alkyl, alkene, alkynyl, acyl, phenacyl or benzoyl, which may be unsubstituted or substituted with other functional groups including, but not limited to halide (e.g., Cl or F), alkyl (e.g., methyl, ethyl, n-propyl, isopropyl), alkoxy (—OCH$_3$ or —OCH$_2$CH$_3$), aryloxy (e.g., —O-phenyl) and the like. For example, such salts may be formed by reacting oltipraz with HCl. In another example, such salts may be formed by reacting oltipraz with an alkyl, alkene, or alkynyl halide such as, methyl chloride, methyl iodide and the like. In another example, such salts may be formed by reaction with an acyl, phenacyl or benzoyl halide (e.g., chloride), such as acetyl chloride, n-butyl chloride, benzoyl chloride and the like.

It also has been found that the (−) rotomer can be prepared (see Examples 2 and 7-11 below) can be present in a substantial rotomeric excess (e.g., up to about 90% or higher, including a 30-40% excess, a 40-50% excess, a 50-60% excess, and a 60-65%, 60-70% and 70-80% excess).

The (−) rotomer oltipraz-complex can be prepared, e.g., as described in Examples 2 and 7-11, by reacting the oltipraz with various carboxy or phosphoric acids and their salts, alkyl and aryl phosphates, alkyl and aryl sulfonic acids and their salts, substituted and unsubstituted thiocarboxy acids and their salts. For example, in the case of the hydroxymaleate oltipraz complex, the oltipraz is reacted with (+)-diacetyl-L-tartaric anhydride in 5 ml of a dry polar solvent such as ultra-dry acetone, followed by the addition of glacial acetic acid. This reaction forms a bond between the alpha nitrogen of the pyrazinyl ring and the oxygen atom of the maleate substantially simultaneously with cyclization rearrangement of the diacetyl tartrate to yield the maleate anhydride ring.

Other complexes of oltipraz that may exhibit a rotomeric preference for the (−) rotomer include those in which a direct bond is formation between the alpha nitrogen of the pyrazinyl ring and an electronegative atom like oxygen, sulfur, or phosphorous that is sufficient to disrupt the hyperconjugation within the molecule. Such oltipraz-complexes may to provide up to 100% rotomeric excess of the (−) rotomer if they can stabilize the (−) rotomer configuration through disruption of the above-described hyperconjugation and/or increased steric strain. For example, such oltipraz-complexes can provide a rotomeric excess of the (−) rotomer in an amount selected from the group consisting of at least 30%, at least 40%, at least 50%, at least 60%, at least 70%, at least 80%, at least 90%, at least 95%, at least 96%, at least 97%, at least 98%, or at least 99%. The rotomeric excess of (−) rotomer thus can be, e.g., an amount selected from the group consisting of a 30-40% excess, a 40-50% excess, a 50-60% excess, a 60-65% excess, a 60-70% excess, a 70-80% excess, an 80-90% excess, and a 90-100% excess. Such oltipraz complexes include those formed by reacting the oltipraz with various carboxy or phosphoric acids and their salts, alkyl and aryl phosphates, alkyl and aryl sulfonic acids and their salts, e.g., substituted and unsubstituted thiocarboxy acids and their salts, e.g., lactic acid, tartronic acid, isothionic acid, isoserine, 2-mercaptoethane sulfonic acid, taurine, propyl phosphonic acid, 2-aminoethylphosphonic acid, diethyl dithiophosphate, diethyl thiophosphate, dimethyl phosphate. It should be noted that it does not appear possible to induce 5-(pyrazin-2-yl)-3H-1,2-dithiole-3-thiones into a configuration like that of oltipraz's (−)

rotomer by changing the size of the substituent on the 4-position of the dithiol thione ring (which is a methyl group in oltipraz).

In addition, or in the alternative, to hyperconjugation involving the alpha nitrogen of the pyrazinyl ring, hyperconjugation also can be affected by forming oltipraz-complexes with the meta nitrogen of the pyrazinyl ring. Such (−) rotomeric complexes can be formed via a bond between the meta nitrogen atom and a carbon, oxygen, sulfur or phosphorous atom. This bond can be made to occur singly or together with complexation involving the alpha (ortho) nitrogen atom on the pyrazinyl ring.

As oltipraz conformers are understood to be distributed as a function of their relative energies in a Boltzmann distribution, one means of obtaining a higher rotomeric excess of the individual oltipraz rotomer (or the individual rotomer of an oltipraz-complex) that is most stable under any given set of conditions (e.g., specific solvent), includes cooling a solution of a desired oltipraz composition (e.g., below room temperature such as −78° C. or less) and providing sufficient time for the rotomers to substantially equilibrate. Under such conditions a greater number of molecules will be in more stable (lower energy) conformation(s) than at room temperature. The cooled composition is then dried by evaporation and/or lyophilization, preferably without warming. It has further been found that oltipraz-complexes (e.g., salts) in which either the (−)-rotomer or the (+)-rotomer are in rotomeric excess are able to be substantially purified, e.g., to a purity greater than 90%, greater than 91%, greater than 92%, greater than 93%, greater than 94%, greater than 95%, greater than 96%, greater than 97%, greater than 98%, and greater than 99%. Purification processes and conditions should be chosen so as to minimize the change in the desired rotomeric excess of the composition. For example, the use of temperatures above 40° C. during purification or the use of very polar solvents such as DMSO results in equilibration and substantial loss of the rotomeric excess to close to or equal to zero, whereas the use of chiral chromatography seems to improve rotomeric excess yield. Accordingly, exposing oltipraz-complexes to a chiral media under conditions where one rotomeric form associates with the media more strongly than another rotomeric form, permitting time for the complexes to equilibrate, and eluting the complexes under conditions that do not favor equilibration of the rotomers (e.g., low temperatures), represents a means of enriching for an oltipraz-complex of a desired configuration.

It has further been found that the (+)-rotomer and the (−)-rotomer orientations are not transitional states, but rather are substantially stable configurations when their complexes (e.g., salts) are stored at room temperature such as between 15° C. to 30° C. and 40% to 80% relative humidity, e.g., 20° C. to 25° C. and 50% relative humidity. In this context, "substantially stable" means that the concentrations of the (+)-rotomer and the (−)-rotomer in a composition, as measured by FTIR (as discussed below) within 30 minutes following final purification, will not change by more than an amount selected from the group consisting of 10%, 9%, 8%, 7%, 6%, 5%, 4%, 3%, 2% and 1% when measured using the same FTIR analysis 4 weeks following the final purification.

Pharmaceutical Compositions Comprising the Rotomer Compositions

The rotomer compositions described above can be prepared as pharmaceutical compositions, either as (i) one or more oltipraz-complexes (e.g., salts) comprising a rotomeric excess of the (+)-rotomer, (ii) one or more oltipraz-complexes (e.g., the complexes of Examples 2 and 7-11) comprising a rotomeric excess of (−)-rotomer, or (iii) mixtures of (i) and (ii). Pharmaceutical compositions (i)-(iii) above are referred to herein as "rotomer pharmaceutical compositions." Such rotomer pharmaceutical compositions can be administered in a dry or liquid composition. Formulations of the rotomer pharmaceutical compositions for oral administration also may be presented as a mouthwash, or a carbonated liquid, or an oral spray or aerosol, or an oral ointment, gel, or cream.

In certain aspects, liquids suitable for formulating the rotomer pharmaceutical compositions for oral administration, e.g., buccal administration, may include aqueous and non-aqueous carriers, e.g., water; saline; buffer solutions; organic solvents such as alcohols (e.g., ethanol), glycols, aliphatic alcohols; mixtures of water and organic solvents, and mixtures of organic solvents (optionally also with water); lipid-based materials, polysaccharide-based materials, and other vehicles and vehicle components that are suitable for administration to the oral cavity, as well as mixtures of buccal vehicle components as identified above or otherwise known to the art.

Liquid dosage forms useful for oral administration include pharmaceutically acceptable emulsions, microemulsions, suspensions, syrups and elixirs. In addition to the active ingredients, the liquid dosage forms may contain inert diluents commonly used in the art. Besides inert diluents, the oral compositions can also include adjuvants such as wetting agents, emulsifying and suspending agents (for emulsions and suspensions), sweetening, flavoring, coloring, perfuming and preservative agents.

Alternative aspects of rotomer pharmaceutical compositions suitable for oral administration of the rotomer pharmaceutical compositions include compositions in the form of capsules (including sprinkle capsules and gelatin capsules), sachets, stickpacks, pills, tablets, lozenges, lyophile, powders, granules, implantable compositions, or as a solution or a suspension in an aqueous or non-aqueous liquid, including, e.g., compositions suitable for injection or infusion, or as an oil-in-water or water-in-oil liquid emulsion, or as an elixir or syrup, or as pastilles and/or as mouth washes and the like, each containing a predetermined amount of a composition comprising a quantity of the rotomer pharmaceutical compositions as described herein as the active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), a composition comprising a quantity of the rotomer pharmaceutical compositions can be mixed with one or more pharmaceutically acceptable carriers, and/or any of fillers or extenders, binders, humectants, disintegrating agents solution retarding agents, absorption accelerators, wetting agents, absorbents, lubricants, complexing agents, and coloring agents. The rotomer pharmaceutical compositions may further include components adapted to improve the stability or effectiveness of the formulation. In the case of capsules (including sprinkle capsules and gelatin capsules), tablets and pills, the rotomer pharmaceutical compositions may also comprise buffering agents. Solid compositions of a similar type may also be employed as fillers in soft and hard-filled gelatin capsules using known excipients.

The tablets, and other solid dosage forms of the rotomer pharmaceutical compositions may optionally be scored or prepared with coatings and shells, such as enteric coatings and other coatings well known in the art. They may also be formulated so as to provide slow or controlled release of the active ingredient therein to provide the desired release profile. These compositions may also optionally contain opacifying agents and may be of a composition that they release the active ingredient(s) only, or preferentially, in a certain portion of the gastrointestinal tract, optionally, in a delayed manner. The active ingredient can also be in microencapsulated form, if appropriate, with one or more of the above-described excipients.

Rotomer Pharmaceutical Compositions for Topical Administration

In some aspects, the rotomer pharmaceutical composition may be incorporated into formulations that may be suitable for topical administration, and may include moisturizers, humectants, and other known additives for topical administration. The topical compositions also may be delivered transdermally via a patch that is applied over the skin, and such patches are well known in the art. Persons of skill in the art will recognize other topical delivery compositions and vehicles that may be used.

Rotomer Pharmaceutical Compositions for Rectal/Colonic Delivery

In certain aspects, the rotomer pharmaceutical compositions described above can be formulated for rectal administration to provide colon-specific delivery using known methods and compositions. Generally speaking, delivery of rotomer pharmaceutical composition via rectal administration route can be achieved by using suppositories, enemas, ointments, creams or foams. Suppositories are among the most common rectal dosage forms, and bases are generally fatty in nature, but water-soluble or water-miscible bases can also be utilized. In order to achieve a desirable bioavailability, the active ingredient should come in contact with the rectal or colonic mucosa.

Suitable excipients that are known for preparing compositions suitable for rectal administration include, but not limited to, vehicle, preservatives, surfactants, emulsifiers, mineral oils, propellants, thickening agents, lubricants, preservatives, pH adjusting agents, chelating agents, emollients and/or humectants, permeation enhancers, suspension-forming agents or mucoadhesive agents or combinations thereof. The vehicle may include aqueous, non-aqueous or hydroalcoholic components that are known to be compatible with the rectal and colonic mucosa.

Alternatively, colonic absorption can be accomplished through oral administration of the rotomer pharmaceutical compositions, which compositions are designed to release the active oltipraz in the colon. Such compositions can be in an oral dosage form, e.g., a pill, capsule or liquid, that provides delayed release until the dosage form is in the colon Rotomer Pharmaceutical Compositions and Devices for Inhalation Administration In other aspects, rotomer pharmaceutical compositions described above may be delivered via the respiratory tract by providing the composition in inhalable form, e.g., in an inhaler device, either in dry powder form or in a liquid carrier. For example, inhalable compositions can comprise the active rotomer pharmaceutical composition in dry powder compositions provided in dry powder inhalers. See, e.g., WO2014177519 and US20140065219. Alternatively, inhalable compositions can comprise the active ingredient in a liquid carrier such as ethanol. See, e.g., EP2536412 A2.

The disclosure thus also provides a kit comprising (i) a rotomer pharmaceutical composition as described above, and (ii) a device for administering such composition by inhalation. The kit optionally further contains instructions for use.

Devices for Oral Administration

In certain aspects, liquid formulations of the rotomer pharmaceutical compositions for oral administration may be prepared and administered using a device that facilitates administration of a single dose of the rotomer pharmaceutical composition. Such devices, which are known in the art, can include a cavity or reservoir where a dry composition and a liquid such as water and/or a non-aqueous solvent may be mixed and then administered to the patient via an opening in the device. Typically, such devices comprise a cavity and a compartment that is separate from the cavity, in which compartment a dry powder can reside. At the time of administration, the powder is released from the compartment into the cavity or reservoir. In some devices, this is accomplished by breaking a barrier that separates the compartment from the cavity or reservoir. Thereafter, the powder may be mixed, typically by shaking, with a liquid in the cavity that may have been added earlier or at the time. The cavity is of sufficient size to hold both the dry rotomer pharmaceutical composition and a quantity of liquid comprising an amount of water and/or non-aqueous solvent sufficient to permit mixing of the dry rotomer pharmaceutical composition to form a liquid composition. The liquid may be added to the container at the time of packaging to create a self-contained product comprising both dry composition and liquid that may be mixed together at the time of administration. Alternatively, the container can contain only a dry rotomer pharmaceutical composition and the liquid is then added prior to administration. The liquid may contain flavoring additives as discussed below. Alternatively, other types of packaging that separate the dry and liquid ingredients may be used. For example, the powder and the liquid can be sealed in 2 form-fill-and-seal pouches, either side by side or one on top of the other and separated by a rupturable seal. The person administering the drug would then rupture the seal and mix the contents back and forth between the 2 compartments until dissolved or suspended.

Once the composition is substantially homogeneous (e.g., from the shaking), it is then administered to the patient via an opening in the device created, e.g., by uncoupling a portion of the device to expose the cavity containing the liquid mixture. For example, a portion of the device, e.g., the top, can be removed by unscrewing a threaded portion from another threaded portion of the container to expose the cavity containing the liquid mixture, which then may be administered to the patient or by the patient. Examples of such devices are provided in U.S. Pat. No. 6,148,996, U.S. application 20080202949, and U.S. Pat. No. 3,156,369. Such single-use devices can be employed for orally administering liquid compositions described herein, especially for prophylaxis or treatment of oral mucositis or its symptoms as described below.

The disclosure thus also provides a kit comprising (i) a rotomer pharmaceutical composition as described above, (ii) a device for oral administration of such compositions. The kit optionally further contains instructions for use.

For such devices, the rotomer pharmaceutical composition may be in a dry form. In such instances, the dry composition which can be present together, e.g., in a compartment as described above, is admixed with water and/or other liquid solvent prior to administration (e.g., by exposing the dry composition to the liquid and shaking) as discussed above.

Methods of Treating

In certain aspects, the rotomer pharmaceutical compositions and devices described above may be used for treating a human or non-human animal patient in need. The patient typically will be a human patient, although the rotomer pharmaceutical compositions of this disclosure can be used for treating non-human animals, e.g., for veterinary uses. The compositions of this disclosure may be used for preventing or treating a wide variety of diseases and conditions, including diseases and conditions for which treatment with oltipraz is known. Examples of such diseases and conditions include mucositis, HIV, cancers, hepatitis (including HBV and HCV), keratin-based skin diseases, including skin blistering and epidermolysis bullosa simplex and related diseases, dermatitis, inflammatory disorder or disease (including endothelial dysfunction and cardiovascular disease), cachexia, weight loss, sepsis, contrast-induced nephropathy, diabetes, obesity, PCOS, steatosis, hyperlipidemia, and hypertension, chronic kidney disease, pulmonary fibrosis, hypoxic conditions, chemical-induced lung injury, respiratory distress disorder, anon gap acidosis, nephritis, lupus, interstitial lung disease, graft dysfunction, hepatitis, acute kidney injury, noise-induced hearing injuries, poison ingestion, retinopathy, neurotoxicity, cancer-induced injury such as ototoxicity, respiratory infections, autism, conditions involving vasospasm, and conditions considered treatable by provision of n-acetylcysteine, injectable reduced glutathione, or a known intracellular glutathione enhancing agent.

Typically, the rotomer pharmaceutical composition is provided to the patient in an effective amount. The term "effective amount" is used herein to refer to an amount of the rotomer pharmaceutical composition sufficient to produce a significant biological response (e.g., a significant decrease in inflammation). Actual dosage levels of the rotomer pharmaceutical compositions can be varied so as to administer an amount that is effective to achieve the desired therapeutic response for a particular subject and/or application. Of course, the effective amount in any particular case will depend upon a variety of factors including formulation, route of administration, combination with other drugs or treatments, severity of the condition being treated, and the physical condition and prior medical history of the subject being treated.

As used herein, the term "subject" includes both human and animal subjects, and thus veterinary therapeutic uses are provided in accordance with this disclosure. The terms "treatment" or "treating" relate to any treatment of a condition of interest (e.g., mucositis, an inflammatory disorder or a cancer), including but not limited to prophylactic treatment and therapeutic treatment. As such, the terms "treatment" or "treating" include, but are not limited to: preventing a condition of interest or the development of a condition of interest; inhibiting the progression of a condition of interest; arresting or preventing the further development of a condition of interest; reducing the severity of a condition of interest; ameliorating or relieving symptoms associated with a condition of interest; and causing a partial, substantially complete, or complete regression of a condition of interest or one or more of the symptoms associated with a condition of interest.

The rotomer pharmaceutical compositions and devices described above are suitable for treating patients who are suffering from mucositis or who will undergo a treatment such as radiation treatment or chemotherapy that can lead to mucositis, e.g., in the oral cavity (including in the buccal cavity), in the alimentary canal, in the colon and/or rectum, and/or on the skin. Where the mucositis is oral mucositis, the compositions and devices described above for oral delivery may be preferred. Such patients, e.g., may be undergoing, or about to undergo chemotherapy and/or radiation therapy, e.g., radiation treatment in the head and neck area, or to another area of the body.

The rotomer pharmaceutical compositions and devices above may be used to accomplish one, more than one, or all of the following beneficial effects on human or non-human animal patients, i.e., (i) prophylactically prevent or delay the onset of mucositis, including oral mucositis (e.g., inflammation of the mucosa), (ii) treat existing mucositis, including oral mucositis (iii) alleviate symptoms associated with mucositis, including oral mucositis (iv) reduce or lessen the severity of existing mucositis, including oral mucositis (v) hasten the cure or healing of mucositis, including oral mucositis (vi) reduce the incidence and/or duration of mucositis, including oral mucositis, e.g., mild, moderate and severe oral mucositis, (vii) prophylactically prevent or delay the onset of weight loss or cachexia by a patient with oral mucositis, (viii) reduce the amount of weight loss or cachexia experienced by a patient with oral mucositis, and/or (ix) increase the ability of a patient with oral mucositis to take food by mouth. Such compositions also may be used for the prevention and/or treatment of patients with dysphagia (difficulty swallowing), e.g., cancer patients, or to delay the onset of dysphagia or lessen the severity of dysphagia, e.g., in cancer patients. Such compositions also may be used for the prevention and/or treatment of patients with xerostomia (the subjective feeling of oral dryness), or to delay the onset of xerostomia, lessen the severity of xerostomia, and/or reduce the incidence of moderate-to-severe xerostomia. In certain aspects, the single-use devices described above may be used for administration of liquid compositions for accomplishing one, more than one, or all of the above relating to oral mucositis, dysphagia and xerostomia. Advantageously, formulations are also non-irritating, well-tolerated, palatable (if orally administered), non-cytotoxic, weakly or non-sensitizing, non-sensitizing.

Certain aspects herein provide methods for treating mucositis, comprising administering to a patient in need thereof a therapeutically effective amount of a rotomer pharmaceutical composition as described herein. The disclosure also provides a rotomer pharmaceutical composition as described herein for use in the treatment of mucositis. The disclosure also provides the use of a rotomer pharmaceutical composition as described herein in the manufacture of a medicament for the treatment of mucositis. The administration of the formulation to a patient may be an oral administration, including buccal administration. The methods of administration described herein can represent a treatment regimen of a predetermined duration, e.g., 1 month, 2 months, 3 months, 4 months, 5 months, 6 months, or longer. Rotomer pharmaceutical compositions according to this disclosure can be applied or administered once daily, twice daily, three times daily, or as needed. In situations where the patient is undergoing chemotherapy and or radiation therapy, the dosage may be administered prior to a treatment, e.g., within 1 hour, within 3 hours, within 6 hours, within 12 hours, within 24 hours, or more than 24 hours before the treatment. For example, dosing can begin several days in advance of receiving chemotherapy, radiation therapy and/or chemoradiation therapy. For example, the patient can begin receiving treatment once per day, or more than once per day, beginning three days in advance of starting therapy, and then receive dosing each day during the course treatment, including days when therapy is not received. On days when treatment is being given, e.g., dosing is given prior to therapy, e.g., within an hour before therapy is administered. Dosing can be given anytime during the day, e.g., in the morning, on days when therapy is not received. Additionally, or alternatively, the dosage may be administered after a treatment, e.g., within 1 hour, within 3 hours, within 6 hours, within 12 hours, within 24 hours after the treatment, or more than 24 hours after the treatment.

This disclosure thus provides methods for treating mucositis comprising administering to a patient in need thereof a therapeutically effective amount of a rotomer pharmaceutical composition described above. The disclosure also provides rotomer pharmaceutical compositions as described above for use in the treatment of mucositis. The disclosure also provides the use of a rotomer pharmaceutical composition as described herein in the manufacture of a medicament for the treatment of mucositis. The administration of the rotomer pharmaceutical composition to a patient may be an oral administration, including buccal administration.

Where liquid compositions are administered, the composition may be administered orally or parenterally, e.g., by subcutaneous, intramuscular, intrasternal, or intravenous injection. Where oral administration is employed, the liquid composition simply may be swallowed, or it may be administered by a "swish and swallow" regimen or a "swish and spit" regimen. By administering the composition orally in a liquid form to a patient who has oral mucositis or who is at risk of developing oral mucositis (e.g., undergoing or about to undergo chemotherapy, radiation therapy and/or chemradiation therapy), the compositions may provide a therapeutic benefit in terms of the mucositis as described above, i.e., it may prophylactically prevent or delay the onset of mucositis, treat existing mucositis, alleviate or decrease symptoms associated with mucositis (e.g., inflammation and bleeding of the mucosa), reduce or lessen the severity of existing mucositis, reduce the duration of the mucositis, and/or hasten the reduction, cure or healing of mucositis. In such cases, liquid compositions comprising an ingredient with a negative charge, e.g., a cationic surfactant or polymer such as Eudragit RL, may provide a further advantage by virtue of providing an adherence or association with the mucosa of the mouth, which tends to have a positive charge. The physical and chemical properties of aspects of the compositions described herein can impart characteristics to the formulation such as stability, delivery of the active agent to the mucosal membrane, and ease of administration.

As noted above, the rotomer pharmaceutical compositions as described herein may be co-administered with other therapeutic agents, either together or separately as part of a therapeutic regimen. Such agents include N acetylcysteine and/or other antioxidants, pantothenic acid (vitamin B5) or other agents that enhance glutathione synthesis, glutathione, e.g., for topical administration, Medihoney (for topical administration), curcumin (for topical administration) or other NF-kappaB inhibitors, Mesalamine and/or other anti-inflammatory agents, e.g., for oral or rectal administration compositions, and superoxide dismutase or other compounds that prevent damage from reactive $O_2^-$ (superoxide).

EXAMPLES

Certain aspects of this disclosure are further illustrated by the following examples, which should not be construed as limiting the scope of the appended claims in any way.

Example 1: Method to Make the Hydrochloride of Oltipraz: (+) Rotomer 20 mg of synthesized oltipraz powder (ST-617-API, discussed below) is recrystallized using acetonitrile:water and added into a 5 ml glass vial equipped with a rubber septum. To the vial is added 1 ml of dry chloroform at room temperature and the vial set on a vibrating table until the solution is clear. Using a gas syringe, 5 ml of anhydrous hydrochloric acid gas is slowly bubbled into the solution over 5 minutes with intermittent shaking of the vial. Once all the HCl gas has been added, the vial is shaken for 5 minutes, the septum is removed, and the solvent gently evaporated under a slow steady stream of nitrogen gas to give the hydrochloride complex of oltipraz as an orange/red solid. FTIR: C=S peaks 1203/1211 (relative intensity 3:7) and 433/421 (relative intensity 2:8).

Figure 5:
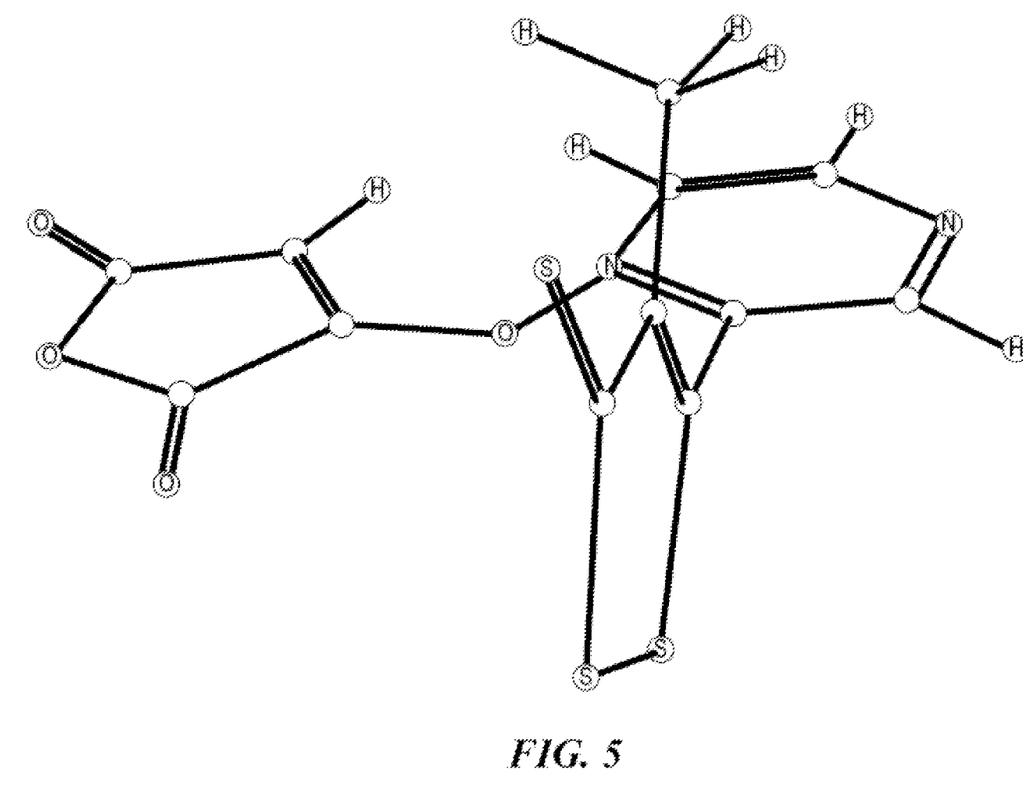
FIG. 5 depicts the hydroxymaleate anhydride complex of oltipraz.

Example 2: Method to Make Hydroxymaleate Anhydride Complex of Oltipraz: (−)-Rotomer 20 mg of synthesized oltipraz powder is recrystallized using acetonitrile:water and added into a 10 ml glass vial equipped with a rubber septum. All moisture is removed from the vial by nitrogen gas using a gas syringe. The vial is placed in an ice-bath and into it is added a pre-chilled (10° C.) solution of 22 mg of (+)-diacetyl-L-tartaric anhydride in 5 ml of ultra-dry acetone, shaken on a vibrating table for 5 minutes, and after 5 minutes is added 0.5 ml of glacial acetic acid over 30 seconds, using a syringe. After 4 h at 0-10° C. with intermittent shaking, the vial is allowed to come to room temperature. The septum is removed, and the solvent gently evaporated under a slow steady stream of nitrogen gas to give the hydroxymaleate anhydride complex of oltipraz (see FIG. 5) as orange solid. The complex is washed 3 times with ethyl ether to remove traces of acetic acid. FTIR: C=S peaks 1201/1214 (relative intensity 8:2) and 434/423 (relative intensity 8:2). A 2 mg sample of the oltipraz-complex is ground with KBR and made into a standard pellet for FTIR analysis on a Perkin Elmer 1600 series FTIR.

Example 3: Method to Make the Acetyl Chloride Complex of Oltipraz: (+) Rotomer 20 mg of synthesized oltipraz powder is recrystallized using acetone:water and added into a glass vial equipped with a rubber septum. To the vial was added 10 ml of dry chloroform at room temperature and the vial set on a vibrating table until the solution is clear. Using a syringe, 5 ml of anhydrous acetyl chloride is slowly added into the solution with intermittent shaking of the vial. Once all the acetyl chloride has been added, the vial is shaken for 15 minutes, the septum is removed, and the solvent and excess reagent gently evaporated under a slow steady stream of nitrogen gas to give the acetyl chloride complex of oltipraz as an orange solid. FTIR: C=S peaks 1202/1212 (relative intensity 3:7) and 432/422 (relative intensity 2:8).

Example 4: Method to Make the n-Butyl Chloride Complex of Oltipraz: (+) Rotomer 20 mg of synthesized oltipraz powder is recrystallized using acetone:water and added into a glass vial equipped with a rubber septum. To the vial was added 10 ml of dry chloroform at room temperature and the vial set on a vibrating table until the resulting solution is clear. Using a syringe, 5 ml of n-butyl chloride is slowly added into the solution with intermittent shaking of the vial. Once all the n-butyl chloride has been added, the vial is warmed to 65° C. and shaken for 30 minutes, the septum is removed, and the solvent and excess reagent gently evaporated under a slow steady stream of nitrogen gas to give the n-butyl chloride complex of oltipraz as a red solid. FTIR: C=S peaks 1201/1213 (relative intensity 2:8) and 433/421 (relative intensity 2:8).

Example 5: Method to Make the Methyl Iodide Complex of Oltipraz: (+) Rotomer 50 mg of synthesized oltipraz powder is recrystallized using acetone:water and added into a pressure-rated glass vial equipped with a screw seal. To the vial was added 20 ml of dry chloroform at room temperature and the vial set on a vibrating table until the resulting solution is clear. Using a syringe, 10 ml of methyl iodide is slowly added into the solution with intermittent shaking of the vial. Once all the methyl iodide has been added, the vial is sealed and heated to 120° C. under pressure and shaken for 3 hours ("hrs"), the vial is cooled and unsealed, and the solvent and excess reagent gently evaporated under a slow steady stream of nitrogen gas to give the methyl iodide complex of oltipraz as a red/brown solid. FTIR: C=S peaks 1197/1214 (relative intensity 2:8) and 431/419 (relative intensity 2:8).

Example 6: Method to Make the Benzoyl Chloride Complex of Oltipraz: (+) Rotomer 20 mg of crude oltipraz powder is added into a glass vial equipped with a rubber septum. To the vial was added 10 ml of dry chloroform at room temperature and the vial set on a vibrating table until the resulting solution is clear. Using a syringe, 1 ml of anhydrous benzoyl chloride is slowly added into the solution with intermittent shaking of the vial. Once all the benzoyl chloride has been added, the vial is shaken for 15 minutes, the septum is removed, and the solvent and excess reagent gently evaporated under 10 mm Hg vacuum to give the benzoyl chloride complex of oltipraz as a red solid. FTIR: C=S peaks 1200/1213 (relative intensity 3:7) and 431/419 (relative intensity 3:7).

Example 7: Method to Make the Diethyl Dithiophosphate Complex of Oltipraz: (−) Rotomer 22 mg of synthesized oltipraz powder is recrystallized using acetone:water and added into a glass round bottom flask equipped with a magnetic stirrer and cold-water condenser. To the flask was added 10 ml of acetone at room temperature and 20 mg of diethyl dithiophosphate ammonium salt is slowly added into the solution while stirring is continued. Once all the diethyl dithiophosphate has been added, the temperature is increased and set to reflux for 3 hrs. Released ammonia is captured in a dilute hydrochloric acid trap from the top of the condenser. After 3 hrs the solvent is removed to yield the diethyl dithiophosphate complex of oltipraz as an orange/red solid. FTIR: C=S peaks 1201/1220 (relative intensity 9:1) and 472/444 (relative intensity 8:2)

Example 8: Method to Make the Diethyl Thiophosphate Complex of Oltipraz: (−) Rotomer 22 mg of synthesized oltipraz powder is recrystallized using acetone:water and added into a glass round bottom flask equipped with a magnetic stirrer and cold-water condenser. To the flask was added 10 ml of acetone at room temperature and 19 mg of diethyl thiophosphate ammonium salt is slowly added into the solution while stirring is continued. Once all the diethyl thiophosphate has been added, the temperature is increased and set to reflux for 3 hrs. Released ammonia is captured in a dilute hydrochloric acid trap from the top of the condenser. After 3 hrs the solvent is removed to yield the diethyl dithiophosphate complex of oltipraz as an orange/red solid. FTIR: C=S peaks 1208/1221 (relative intensity 9:1) and 479/442 (relative intensity 9:1).

Example 9: Method to Make the Dimethyl Phosphate Complex of Oltipraz: (−) Rotomer 175 mg of trimethyl phosphate was placed with 100 mg of crude oltipraz (95% purity), in a round bottom flask equipped with a condenser and stirrer and heated at 80° C. for 72 hr. After 72 hrs, the mixture is cooled to room temperature and washed with 50 ml of toluene five times. 255 g of orange/red dimethyl phosphate complex of N-methyl oltipraz is collected from the lower layer and dried under vacuum at 60° C. FTIR: C=S peaks 1210/1227 (relative intensity 9:1) and 489/453 (relative intensity 9:1).

Example 10: Method to Make the Isethionic Acid Complex of Oltipraz: (−) Rotomer 22 mg of crude oltipraz powder is added into a glass round bottom flask equipped with a magnetic stirrer and cold-water condenser. To the flask was added 10 ml of acetone at room temperature and 30 mg of isethionic acid ammonium salt is slowly added into the solution while stirring is continued. Once all the isethionic acid ammonium salt has been added, the temperature is increased and set to reflux for 6 hrs. Released ammonia is captured in a dilute hydrochloric acid trap from the top of the condenser. After 6 hrs the reaction is brought to pH 6.8 with minimum quantity of concentrated hydrochloric acid and the resultant mixture is evaporated, under vacuum, to dryness to yield the isethionic acid complex of oltipraz as a red/brown solid. FTIR: C=S peaks 1216/1228 (relative intensity 9:1) and 464/435 (relative intensity 9:1).

Example 11: Method to Make the Thiobenzoic Acid Complex of Oltipraz: (−) Rotomer 20 mg of crude oltipraz powder is added into a glass vial equipped with a rubber septum. To the vial was added 10 ml of dry chloroform at room temperature and the vial set on a vibrating table until the resulting solution is clear. Using a syringe, 1 ml of thiobenzoic acid ammonium salt is slowly added into the solution with intermittent shaking of the vial. Once all the thiobenzoic acid ammonium salt has been added, the temperature is increased and set to reflux for 1 hr. The released ammonia is captured in a dilute hydrochloric acid trap from the top of the condenser. After 1 hour the contents are removed under vacuum to yield the thiobenzoic acid complex of oltipraz as an orange solid. FTIR: C=S peaks 1210/1223 (relative intensity 9:1) and 474/438 (relative intensity 9:1)

Example 12: Effect of (+) and (−) Rotomers on ROS Production in $H_2O_2$-Induced Oxidatively Stressed HGEPp Cells The formation of reactive oxygen species (ROS) is indicative of oxidative stress. Accumulation of ROS coupled with an increase in oxidative stress is implicated in the pathogenesis of many diseases, one of which is mucositis. See, Sonis, *A biological approach to mucositis*, J Support Oncol 2004; 2:21-36; Halliwell & Whiteman, *Measuring reactive* species and oxidative damage in vivo and in cell culture: how should you do it and what do the results mean?, British J. Pharmacology, Volume 142, Issue 2, May 2004, 231-255; and Iglesias-Bartolome et al., *mTOR Inhibition Prevents Epithelial Stem Cell Senescence and Protects from Radiation-Induced Mucositis*, Cell Stem Cell 11, 401-414, Sep. 7, 2012). Free radicals and other reactive species are constantly generated in vivo and cause oxidative damage to biomolecules, a process held in check by multiple antioxidant and repair systems.

An assay to determine the effect of oltipraz and formulated oltipraz crystals on intracellular ROS using HGEPp cells is described in Example 7 of PCT/IB2017/001312, published as WO 2018/047013 to Applicant ST IP Holding AG. The formulated oltipraz crystals were prepared generally according to the process described in Example 1 of PCT/IB2017/001312 (MHD less than about 350 nm). That same assay was carried out on the rotomer compositions prepared in Examples 1-11 above to determine their effect on protecting primary human gingival epithelial cells (HGEPp) cells from oxidative damage induced by hydrogen peroxide ($H_2O_2$).

| | Conditions: |
|---|---|
| Normal | normal control cells were cultured in DPBS containing 0.3% DMSO. |
| Positive control (PC) | oxidative stressed cells after treatment with 0.3 mM $H_2O_2$ for 4 h. |
| Formulated oltipraz crystals (ST-617-DPI) | group of cells pretreated for 24 hrs with ST-617-DPI at 100 µg/mL prior to treatment with $H_2O_2$. |
| (+) rotomer complexes | group of cells pretreated for 24 hrs with (+) rotomer complex at 100 µg/mL prior to treatment with $H_2O_2$. |
| (−) rotomer complexes | group of cells pretreated for 24 hrs with (−) rotomer complex at 100 µg/mL prior to treatment with $H_2O_2$ |

Results:

The results of the above assay on ST-617-DPI and the rotomer complexes of Examples 1-11 are shown below in Table 1. The result for ST-617-API (recrystallized oltipraz prepared according to the process disclosed in WO2016207914) reported in Table 1 below is taken from FIG. 9 of PCT/IB2017/001312 (100 µg/mL pretreatment).

TABLE 1

| Normal | 100% (optical density baseline) |
|---|---|
| Positive control (PC) | 139% |
| Recrystallized oltipraz (ST-617-API) | 124% |
| Formulated oltipraz crystals (ST-617-DPI) | 122% |
| Example 1 | 128% |
| Example 2 | 116% |
| Example 3 | 129% |
| Example 4 | 128% |
| Example 5 | 134% |
| Example 6 | 131% |
| Example 7 | 117% |
| Example 8 | 115% |
| Example 9 | 112% |
| Example 10 | 113% |
| Example 11 | 116% |

The reduction in ROS levels for the group of cells treated with 100 µg/mL of ST-617-DPI in the assay (122%) as compared to the control (139%) were consistent with the results reported in PCT/IB 2017/001312 for 100 µg/mL (123%), and with other results obtained for the ST-617-DPI in this assay. The (+) rotomer complexes provided a modest decrease in ROS whereas the (−) rotomer complexes provided a substantial decrease. The assay results for the (−) rotomer were statistically significant at a 90% confidence level.

Example 13: Differentially Regulated Oxidative Stress-Related Genes in HGEPp Cells Following Treatment with ST-617-DPI, ST-617-API and the Rotomer Complexes of Examples 1-11

The Nrf2 system (discussed above) is considered to be a major cellular defense mechanism against oxidative damage by activating genes that encode phase II detoxifying and antioxidant enzymes. One such oxidative damage is oral mucositis which occurs during and after chemotherapy treatment particularly in head and neck cancer treatments. The Human oxidative stress PCR array was used to evaluate the relative expression of 84 stress genes after pretreating with 100 ug/ml of formulated oltipraz composition prepared generally in accordance with the process described in Example 1 of PCT/IB2017/001312 (MHD less than about 350 nm), the rotomeric complexes described in Examples 1-11 above, and negative control (formulated oltipraz composition without the oltipraz) within HGEPp cells.

Materials

HGEPp cells were purchased from CellnTec Advanced Cell Systems AG. RNEasy Plus Micro Kit was purchased from Qiagen N.V., USA. RNase-free DNase Set was purchased from Qiagen N.V., USA. RT2 Easy First Strand Kit (DNA generator) and RT2 SYBR® Green fluor qPCR mastermix were purchased from Qiagen N.V., USA. Oxidative Stress RT2 profiler PCR arrays (84 protective genes) were purchased from Qiagen N.V., USA. The iCycler PCR system from Bio-Rad Inc., USA was used for the RT-PCR.

Methods

Cell Culture:
Pooled primary HGEPp cells were propagated in CnT-Prime epithelial culture medium provided by CellnTec on 100 mm petri dishes coated with 30 mg/ml Type I rat tail collagen (BD Biosciences) diluted in Dulbecco's phosphate-buffered saline (DPBS). HGEPp cells were grown in 12×60 mm Nunc™ Cell Culture dishes at a 2.5×104 cells/cm2 density concentration.
Preparation of the Dosing Solutions:
Formulated oltipraz crystals (ST-617-DPI) were prepared generally according to the process described in Example 1 of PCT/IB2017/001312. Recrystallized oltipraz was prepared according to the process disclosed in WO2016207914 ST-617-API. The ST-617-DPI, ST-617-API and rotomeric complexes of Examples 1-11 were dissolved in a DMSO to arrive at a final concentration of 100 µg/ml. All dosing solutions contained 0.3% of DMSO which is well below the maximum tolerated DMSO percent of 0.8% for HGEPp cells.
Pre-Treatment of HGEPp Cells with ST-617-DPI and Rotomer Complex Solutions:
1. Dish cell concentration was selected to be 2.5×105/ml to yield an OD absorbance within the linear portion of the control curve.

2. Once the HGEPp cells were cultured and ready (had reached confluence) on the dishes, the media was removed and discarded. The cells were washed gently with DPBS 2-3 times and the last wash removed and discarded.

3. The HGEPp cell culture dishes were then pretreated for 24 h with ST-617-API, ST-617-DPI and the rotomeric complexes at 100 μg/mL concentrations (in duplicate) at 37° C.

mRNA Preparation from HGEPp Cells:

The RNeasy UCP Micro Kit was used to purify mRNA from the HGEPp cells.

1. After discarding and washing treatments, the cells were pelleted by centrifuging for 5 min at 1000 RPM in a centrifuge tube. All the supernatant was carefully removed by aspiration, making sure all the cell medium has been removed thoroughly.

2. The cells were disrupted by adding 350 μl buffer RULT taking care to loosen the cell pellet from the tube and vortexed to mix thoroughly and the mixture was homogenized by passing the lysate 5 times through 20-gauge needle fitted to an RNase-free syringe.

3. Added 350 μl of 70% ethanol to the lysate and it was mixed again by pipetting. (Some precipitate is visible but is not a problem for the assay)

4. Transferred the sample, including any precipitate that may have formed, to an RNeasy UCP MinElute spin column placed in a 2 ml collection tube and centrifuged for 15 s at 10,000 rpm. Discarded the flow through.

5. Added 350 μl Buffer RUWT to the spin column and centrifuged for 15 s at 10,000 rpm to wash the membrane. Discarded the flow thru.

6. Added 10 μl DNase I stock solution to 70 μl Buffered RDD. Mixed gently, added 80 ul of the DNase I mix directly to the spin-column membrane and vortexed for 15 min.

7. Added 350 μl Buffer RUWT to the spin column and centrifuged for 15 s at 10,000 rpm to wash it and discarded the flow thru.

8. Placed the spin column in a new 2 ml collection tube, add 500 μl Buffer RUPE and centrifuged for 15 s at 10,000 rpm. Discarded the flow thru.

9. Washed the spin column again with 500 μl of 80% ethanol and placed it in a new 2 ml collection tube and centrifuge for 5 mins at full speed with the lid open to make sure all ethanol is removed.

10. Placed the spin column in a new 1.5 ml collection tube, added 14 μl ultra-clean water directly to the center of the spin-column membrane, closed the lid and centrifuged for 1 min at full speed to elute the RNA. The dead volume of the spin column is 4 μl. Eluted with 16 μl ultra-clean water to yield a 20 μl (4 μg) RNA eluate.

cDNA Prep for RT-PCR:

1. A RNA sample from each of the above treatments was added to 40 μl of Buffer GE2 (gDNA elimination buffer) and RNase-free $H_2O$ to make a final volume of 60 μl.

2. Incubated at 37° C. for 5 min and immediately placed on ice for 2 minutes.

3. Added 62 μl of the BC5 Reverse Transcriptase Mix to each 60 μl RNA sample for a final volume of 102 μl.

4. Incubated at 42° C. for exactly 15 minutes and then immediately stopped the reaction by heating at 95° C. for 5 minutes. (held on ice until qPCR, if required).

Human Oxidative Stress RT2 Profiler PCR Array:

RT-PCR is a highly sensitive and reliable method for gene expression analysis. The assay was reliably used to analyze expression levels of 84 genes related to oxidative stress in HGEPp cells pre-treated with ST-617-API, ST-617-DPI and the rotomeric complexes at 100 μg/ml for 24 h. The cDNA from above was mixed with the RT2 SYBR Green fluor Mastermix and aliquoted into the wells of the RT2 Profiler PCR Array. RT-PCR was performed on an iCycler. Gene expression was compared using Ct values and the results were calculated using ΔΔ Ct method with normalization to the average expression levels of the five common genes (ACTB, B2M, GAPDH, HPRT, and RPL13A).

Results:

The results of the assays on the ST-617-DPI and rotomer complexes of Examples 1-11 are shown below in Table 2. The results for ST-617-API (recrystallized oltipraz prepared according to the process disclosed in WO2016207914) reported in Table 2 below are from an earlier assay conducted as described above.

TABLE 2

| GENE | ST-617 API | ST-617 DPI | Ex. 1 | Ex. 2 | Ex. 3 | Ex. 4 | Ex. 5 | Ex 6 | Ex. 7 | Ex. 8 | Ex. 9 | Ex. 10 | Ex. 11 | (+) rotomer average | (−) rotomer average |
|---|---|---|---|---|---|---|---|---|---|---|---|---|---|---|---|
| UP REGULATION RELATIVE FOLD CHANGE | | | | | | | | | | | | | | | |
| ALOX12 | 6.15 | 6.42 | 6.38 | 6.46 | 6.33 | 5.82 | 6.04 | 5.93 | 6.38 | 6.41 | 6.43 | 6.48 | 6.39 | 6.07 | 6.43 |
| SOD1 | 2.46 | 4.88 | 3.86 | 5.13 | 4.24 | 4.15 | 3.89 | 3.92 | 4.85 | 4.86 | 5.22 | 5.23 | 4.96 | 4.04 | 5.04 |
| GPX1 | 4.88 | 4.82 | 4.81 | 4.8 | 4.76 | 4.80 | 4.98 | 4.43 | 4.72 | 4.81 | 4.89 | 4.86 | 4.82 | 4.77 | 4.82 |
| NQO1 | 2.95 | 3.67 | 3.14 | 4.07 | 3.36 | 3.34 | 3.15 | 3.17 | 3.93 | 3.92 | 4.24 | 4.26 | 4.09 | 3.24 | 4.09 |
| MPO | | 3.35 | 3.22 | 3.21 | 3.10 | 3.20 | 3.18 | 3.05 | 3.42 | 3.47 | 3.41 | 3.39 | 3.44 | 3.15 | 3.39 |
| GCLC | 4.14 | 3.26 | 3.35 | 4.52 | 3.27 | 3.35 | 3.38 | 3.31 | 4.41 | 4.39 | 4.60 | 4.52 | 4.46 | 3.33 | 4.48 |
| GPX4 | | 2.91 | 2.86 | 2.84 | 2.83 | 2.96 | 2.85 | 2.91 | 2.99 | 3.02 | 2.93 | 2.79 | 2.94 | 2.86 | 2.92 |
| GSTP1 | 2.17 | 2.98 | 2.77 | 3.07 | 2.87 | 2.88 | 2.90 | 2.74 | 3.13 | 3.08 | 3.16 | 3.18 | 3.07 | 2.83 | 3.12 |
| GCLM | 3.03 | 2.19 | 2.33 | 3.01 | 2.38 | 2.38 | 2.27 | 2.25 | 3.00 | 3.02 | 3.15 | 3.11 | 3.08 | 2.32 | 3.06 |
| DOWN REGULATION RELATIVE FOLD CHANGE | | | | | | | | | | | | | | | |
| GTF2i | 0.34 | 0.32 | 0.33 | 0.26 | 0.32 | 0.35 | 0.33 | 0.36 | 0.29 | 0.29 | 0.28 | 0.31 | 0.29 | 0.34 | 0.29 |
| PRDX2 | | 0.29 | 0.31 | 0.26 | 0.33 | 0.32 | 0.32 | 0.31 | 0.28 | 0.28 | 0.27 | 0.28 | 0.27 | 0.32 | 0.27 |
| PTGS1 | 0.22 | 0.24 | 0.28 | 0.23 | 0.29 | 0.27 | 0.28 | 0.28 | 0.21 | 0.23 | 0.21 | 0.22 | 0.22 | 0.28 | 0.22 |
| UCP2 | 0.18 | 0.20 | 0.26 | 0.15 | 0.26 | 0.25 | 0.29 | 0.28 | 0.17 | 0.14 | 0.15 | 0.16 | 0.15 | 0.27 | 0.15 |

The negative control showed no change in any gene regulation. All the rotomers showed higher gene regulating responses for the (−) rotomer over the (+) rotomer. The highest-fold changes between two rotomers were for SOD1, GCLC, GCLM and UCP2. It is noteworthy that GCLC and GCLM genes, which are glutathione (GSH) biosynthesis genes, showed significant consistent differences between the (+) and (−) rotomer. These results correlate with increases in serum GSH observed in patients in a clinical trial who received ST-617-DPI and experienced low oral mucositis development while undergoing radiation therapy for head and neck cancer. The (−) rotomers showed higher gene upregulating responses compared to ST-617-API for ALOX12, SOD1, NQO1, GCLC and GSTP1. The (−) rotomers showed higher gene upregulating responses compared to ST-617-DPI for SOD1, NQO1, GCLC, GSTP1 and GCLM. Within the (−) rotomers, the dimethyl phosphate and isethionic acid complexes (Examples 9 and 10, respectively) showed significantly higher up-regulation compared to ST-617-DPI and ST-617-DPI for SOD1, NQO1, GCLC, GSTP1 and GCLM. The (−) rotomers also showed a differential down-regulation of UCP2 (Mitochondrial uncoupling protein 2, which is involved in the control of mitochondria-derived ROS) compared to ST-617-DPI and ST-617-API.

The rotomer pharmaceutical compositions and methods of administering the rotomer pharmaceutical compositions of this disclosure thus may be used to treat any human or non-human animal patient to decrease intracellular reactive oxygen species (ROS) and/or decrease oxidative stress, including in patients undergoing treatments that provide oxidative stress such as chemotherapy or radiation therapy.

The rotomer pharmaceutical compositions and methods of administering the rotomer pharmaceutical compositions of this disclosure may be used to treat any human or non-human animal patient to provide an antioxidant effect, including in patients undergoing treatments that provide oxidative stress such as chemotherapy or radiation therapy. The rotomer pharmaceutical compositions and methods of administering the rotomer pharmaceutical compositions of this disclosure also may be used to slow the onset, and/or reduce the severity, and/or reduce the duration of oxidative damage in patients (e.g., mucositis, including oral mucositis), including in patients undergoing treatments that provide oxidative damage such as chemotherapy or radiation therapy.

Based on the above results it is further believed that the (+) rotomer, including compositions in which there is a rotomeric excess of the (+) rotomer, may up-regulate genes associated with Nrf2 pathway. Based on the above results, it is further believed that the (−) rotomer, including compositions in which there is a rotomeric excess of the (−) rotomer, may up-regulate genes associated with Nrf2 pathway.

RECITATION OF ASPECTS

1. A composition comprising a rotomeric excess of the (+) rotomer of 4-methyl-5-(pyrazin-2-yl)-3H-1,2-dithiole-3-thione (oltipraz, see FIG. 4A).

2. A composition according to aspect 1, wherein the composition comprises one or more oltipraz-complexes (e.g., one or more salts of oltipraz) having a rotomeric excess of the (+) rotomer.

3. A composition according to aspect 2, wherein the one or more oltipraz-complexes comprise a salt resulting from addition of a group (e.g., reversible addition of HCl, alkyl halides or acyl halides) to the alpha nitrogen of oltipraz's pyrazinyl ring producing a N-substituted pyrazinium ion and an associated anion, resulting from addition of a group to the alpha nitrogen of oltipraz's pyrazinyl ring producing a N-substituted pyrazinium ion and an associated anion.

4. A composition according to aspect 3, wherein the one or more oltipraz-complexes comprise at least one oltipraz-complex formed by the addition to the alpha nitrogen of oltipraz's pyrazinyl ring of one or more reactants selected from the group consisting of alkyl halide, alkenyl halide, alkynyl halide, acyl halide, benzoyl halide, and combinations thereof, (e.g., one or more reactants selected from the group consisting of: HCl, methyl chloride, substituted or unsubstituted methyl, substituted or unsubstituted formyl, substituted or unsubstituted acetyl, substituted or unsubstituted benzoyl, substituted and unsubstituted butyl). Such oltipraz complexes may be formed by reaction of oltipraz with e.g., formyl chloride, acetyl chloride, benzoyl chloride, and n-butyl iodide respectively, methyl iodide, and combinations thereof. In such an aspect the formyl, acetyl, benzoyl and butyl groups may be associated with the nitrogen atoms at the 2 or 4 position of the pyrazine ring, and may bear one or more substituents selected from, for example, halogen (e.g., F or Cl) and/or lower alkyl (C1-C6 alkyl).

5. A composition according to any of aspects 1-4, wherein the rotomeric excess of the (+) rotomer is in a range selected from the group consisting of a 30-40% excess, a 40-50% excess, a 50-60% excess, and a 60-70% excess, 70-80% excess, and greater than 80% excess.

6. A composition comprising an oltipraz-complex wherein the oltipraz-complex has an excess of the (−) rotomer of 4-methyl-5-(pyrazin-2-yl)-3H-1,2-dithiole-3-thione (oltipraz).

7. A composition according to aspect 6, wherein the composition comprises one or more oltipraz-complexes having a rotomeric excess of the (−) rotomer.

8. A composition according to aspect 7, where the at least one of the one or more oltipraz-complexes comprises a direct bond between the alpha nitrogen of the pyrazinyl ring and an electronegative atom.

9. A composition according to aspect 8, wherein the electronegative atom is selected from the group consisting of oxygen, sulfur, and phosphorous.

10. A composition according to any of embodiments 6-9, wherein the one or more oltipraz-complexes comprise a hydroxymaleate oltipraz-complex.

11. A composition according to any of aspects 6-9, wherein the one or more oltipraz-complexes comprise one or more complexes formed by reacting oltipraz with one or more reactants selected from the group consisting of a carboxy acid or a salt thereof, a phosphoric acid or a salt thereof, an alkyl phosphate, an aryl phosphate, an alkyl sulfonic acid or a salt thereof, an aryl sulfonic acid or a salt thereof, a substituted and unsubstituted thiocarboxy acid or a salt thereof, and combinations of one or more of the foregoing, e.g., lactic acid, tartronic acid, isothionic acid, isoserine, 2-mercaptoethane sulfonic acid, taurine, propyl phosphonic acid, 2-aminoethylphosphonic acid, diethyl dithiophosphate, diethyl thiophosphate, dimethyl phosphate.

12. A composition according to any of aspects 6-9, wherein the one or more oltipraz-complexes comprise one or more complexes formed by reacting oltipraz with one or more reactants selected from the group consisting of lactic acid, tartronic acid, isothionic acid, isoserine, 2-mercaptoethane sulfonic acid, taurine, propyl phosphonic acid, 2-aminoethylphosphonic acid, diethyl dithiophosphate, diethyl thiophosphate, dimethyl phosphate, and combinations thereof.

13. A composition according to any of aspects 6-12, wherein the rotomeric excess of the (−) rotomer is in a range selected from the group consisting of a 30-40% excess, a 40-50% excess, a 50-60% excess, a 60-65% excess, a 60-70% excess, a 70-80% excess, an 80-90% excess, and a 90-100% excess.

14. A pharmaceutical composition comprising at least one composition according to any of aspects 1-13, wherein the composition is suitable for administration to a human.

15. A pharmaceutical composition according to aspect 14, wherein the composition is in a form suitable for topical administration.

16. A pharmaceutical composition according to aspect 15, wherein the composition is in a form suitable for rectal administration or for administration by inhalation.

17. A pharmaceutical composition according to aspect 14, wherein the composition is in a form suitable for subcutaneous, intramuscular, intrasternal, or intravenous injection.

18. A pharmaceutical composition according to aspect 14, wherein the composition is in a form suitable for oral administration.

19. A pharmaceutical composition according to aspect 18, wherein the composition is in the form of a powder, pill, tablet, or contained within a capsule.

20. A pharmaceutical composition according to aspect 18, wherein the composition is in a liquid form.

21. A process for treating a human or non-human animal patient in need comprising administering to the patient a pharmaceutical composition according to any of aspects 13-20.

22. A process according to aspect 21, wherein the administration comprises an oral administration.

23. A process according to aspect 21, wherein the administration comprises a buccal administration 24. A process for preventing, treating, ameliorating, lessening the severity and/or shortening the duration of mucositis for a human or non-human animal patient in need comprising orally administering a pharmaceutical composition according to any of aspects 18-20.

25. A process for preventing, treating, ameliorating, lessening the severity and/or shortening the duration of mucositis for a human or non-human animal patient in need comprising orally administering a pharmaceutical composition prepared according to any of aspects 18-20.

26. A process for preventing, treating, ameliorating, lessening the severity and/or shortening the duration of mucositis for a human or non-human animal patient in need comprising orally administering to the patient a pharmaceutical composition according to any of aspects 18-20.

27. A process according to any of aspects 24-26, wherein the mucositis in oral mucositis.

28. A process according to any of aspects 24-26, wherein the mucositis in mucositis of the alimentary canal.

29. A process for preventing, treating, ameliorating, lessening the severity and/or shortening the duration of mucositis or dermatitis for a human or non-human animal patient in need comprising topically administering a composition according to aspect 15.

30. A process for preventing, treating, ameliorating, lessening the severity and/or shortening the duration of mucositis for a human or non-human animal patient in need comprising rectally administering a composition according to aspect 16.

31. A process for preventing, treating, ameliorating, lessening the severity and/or shortening the duration of mucositis for a human or non-human animal patient in need comprising administering by inhalation a composition according to aspect 16.

32. A process according to any of aspects 21-31, wherein the patient is undergoing radiation therapy.

33. A process for making a hydroxymaleate anhydride (−) rotomer of oltipraz, comprising the steps of:

(i) reacting oltipraz with (+)-diacetyl-L-tartaric anhydride in the presence of a dry polar solvent to form a reaction mixture; and (ii) adding acetic acid to the reaction mixture.

What is claimed is:

1. A composition comprising one or more oltipraz-complexes wherein the one or more oltipraz-complexes have an excess of the (−) rotomer of 4-methyl-5-(pyrazin-2-yl)-3H-1,2-dithiole-3-thione (oltipraz).

2. The composition according to claim 1, wherein the composition comprises more than one oltipraz-complex having a rotomeric excess of the (−) rotomer.

3. The composition according to claim 1, wherein at least one of the one or more oltipraz-complexes comprises a direct bond between the alpha nitrogen of the pyrazinyl ring and an electronegative atom.

4. The composition according to claim 3, wherein the electronegative atom is selected from the group consisting of oxygen, sulfur, and phosphorus.

5. The composition according to claim 1, wherein the one or more oltipraz-complexes comprise a hydroxymaleate oltipraz-complex.

6. The composition according to claim 1, wherein the one or more oltipraz-complexes comprise one or more complexes formed by reacting oltipraz with one or more reactants selected from the group consisting of a carboxy acid or a salt thereof, a phosphoric acid or a salt thereof, an alkyl phosphate, an aryl phosphate, an alkyl sulfonic acid or a salt thereof, an aryl sulfonic acid or a salt thereof, a substituted or unsubstituted thiocarboxy acid or a salt thereof, and combinations of one or more of the foregoing.

7. The composition according to claim 1, wherein the one or more oltipraz-complexes comprise one or more complexes formed by reacting oltipraz with one or more reactants selected from the group consisting of lactic acid, tartronic acid, isothionic acid, isoserine, 2-mercaptoethane sulfonic acid, taurine, propyl phosphonic acid, 2-aminoethylphosphonic acid, diethyl dithiophosphate, diethyl thiophosphate, dimethyl phosphate, and combinations thereof.

8. The composition according to claim 1, wherein the rotomeric excess of the (−) rotomer is in a range selected from the group consisting of a 30-40% excess, a 40-50% excess, a 50-60% excess, a 60-65% excess, a 60-70% excess, a 70-80% excess, an 80-90% excess, and a 90-100% excess.

9. A pharmaceutical composition comprising at least one composition according to claim 1, wherein the composition is suitable for administration to a human.

10. The pharmaceutical composition according to claim 9, wherein the composition is in a form suitable for topical administration.

11. The pharmaceutical composition according to claim 9, wherein the composition is in a form suitable for topical, rectal, inhalation, subcutaneous, intramuscular, intrasternal, intravenous injection or oral administration.

12. The pharmaceutical composition according to claim 11, wherein the composition is for oral administration and is in the form of a powder, pill, or tablet, or contained within a capsule.

13. The pharmaceutical composition according to claim 11, wherein the composition is in a liquid form.

14. A process for treating a human or non-human animal patient in need comprising administering to the patient the pharmaceutical composition according to claim 9.

15. The process according to claim 14, wherein the administration comprises an oral or buccal administration.

16. A process for preventing, treating, ameliorating, lessening the severity of and/or shortening the duration of mucositis for a human or non-human animal patient comprising orally administering the pharmaceutical composition according to claim 13.

17. The process according to claim 16, wherein the mucositis is oral mucositis or mucositis in the alimentary canal.

18. A process for preventing, treating, ameliorating, lessening the severity and/or shortening the duration of mucositis or dermatitis for a human or non-human animal patient in need comprising topically administering the pharmaceutical composition according to claim 10.

19. The process according to claim 14, wherein the patient is undergoing radiation therapy.

20. A process for making a hydroxymaleate anhydride (−) rotomer of oltipraz, comprising the steps of:
   (i) reacting oltipraz with (+)-diacetyl-L-tartaric anhydride in the presence of a dry polar solvent to form a reaction mixture; and
   (ii) adding acetic acid to the reaction mixture.

21. The process of claim 14, wherein the patient is a human.

22. The process of claim 16, wherein the patient is a human.

23. The process of claim 18, wherein the patient is a human.

* * * * *